United States Patent
Kelson et al.

(10) Patent No.: US 6,617,574 B2
(45) Date of Patent: Sep. 9, 2003

(54) APPARATUS FOR IN-SITU THICKNESS AND STOICHIOMETRY MEASUREMENT OF THIN FILMS

(75) Inventors: Itzhak Kelson, Tel Aviv (IL); Yuval Levy, Rehovot (IL)

(73) Assignees: TRIUMF; RAMOT, University Authority for Applied Research and Industrial Development Ltd.; The University of British Colombia

( * ) Notice: Subject to any disclaimer, the term of this patent is extended or adjusted under 35 U.S.C. 154(b) by 0 days.

(21) Appl. No.: 09/988,316

(22) Filed: Nov. 19, 2001

(65) Prior Publication Data

US 2002/0050160 A1 May 2, 2002

Related U.S. Application Data

(62) Division of application No. 08/914,822, filed on Aug. 20, 1997, now Pat. No. 6,342,265.

(51) Int. Cl.⁷ ............................ G01D 18/00; G12B 13/00
(52) U.S. Cl. .............................. 250/252.1; 250/339.09
(58) Field of Search .................... 250/559.1, 252.1, 250/269.2, 304, 339.03, 339.09, 341.7, 363.1, 370.02, 452.1, 497.1, 498.1, 503.1, 5

(56) References Cited

U.S. PATENT DOCUMENTS

| | | |
|---|---|---|
| 3,574,650 A | 4/1971 | House |
| 3,748,174 A | 7/1973 | Chen et al. |
| 3,773,548 A | 11/1973 | Baker et al. |
| 3,892,490 A | 7/1975 | Uetsuki et al. |
| 4,024,291 A | 5/1977 | Wilmanns |
| 4,467,198 A * | 8/1984 | Joffe et al. .................. 250/308 |
| 4,578,279 A | 3/1986 | Zingher |
| 4,713,140 A | 12/1987 | Tien |
| 4,771,177 A * | 9/1988 | Brown .................. 250/363.09 |
| 5,009,485 A | 4/1991 | Hall |
| 5,134,295 A * | 7/1992 | Walischmiller ........ 250/455.11 |
| 5,241,366 A * | 8/1993 | Bevis et al. ................. 356/632 |
| 5,486,701 A * | 1/1996 | Norton et al. .............. 250/372 |
| 5,501,637 A * | 3/1996 | Duncan et al. ............. 374/126 |
| 6,116,779 A * | 9/2000 | Johnson et al. ............. 374/161 |

OTHER PUBLICATIONS

Beaudoin M. et al.: "Film Thickness and Composition Monitoring During Growth By Molecular Beam Epitaxy Using Alpha Particle Energy Loss", Applied Physics Letters, vol. 72, No. 25, Jun. 22, 1998, pp. 3288–3290, XP000771132.

Triumf Muonic Hydrogen Collaboration, Fujiwara, M.C. et al.: "Characterization of Solidified Gas Thin Film Targets Via Alpha Particle Energy Loss", Nuclear Instruments & Methods in Physics Research, Section–A; Accelerators, 1997, pp. 159–168 XP004097905.

Kelson, I. et al.: "Recoil Implantation of Alpha Sources for Thickness Measurement of Thin Fims" Journal of Physics, D. Applied Physics, vol. 28, No. 1, Jan. 14, 1995, pp. 100–104, XP000495071.

(List continued on next page.)

*Primary Examiner*—David Porta
*Assistant Examiner*—Christine Sung
(74) *Attorney, Agent, or Firm*—Harness Dickey Pierce PLC (57) ABSTRACT

An apparatus and method for using α-particle energy loss to measure the thickness and stoichiometry of films grown by molecular beam epitaxy and other methods. The apparatus for measuring the thickness of films grown on a substrate in a growth chamber, comprises a protective housing having an aperture opening into the growth chamber, a solid state detector disposed in the protective housing, a shutter for opening and closing the aperture, a shield disposed in the housing between the aperture and the solid state detector for shielding the detector, and a calibration source disposed between the shield and the detector for calibrating the measurements made by the detector. A second calibration source disposed between the shutter and the shield, for measuring deposition on the shield.

5 Claims, 9 Drawing Sheets

OTHER PUBLICATIONS

Kelson, I. et al.: "The Applicability of Implanted Alpha–Source To Thickness And Stoichiometry Measurements of Thin Films", Journal of Physics, D. Applied Physics, vol. 30, No. 1, Jan. 7, 1997, pp. 131–136, XP000688415.

Kelson, I. et al.: "A Monoenergetic Electron Source Generated by Nuclear Stimulated Desorption", Journal of Physics, D, vol. 27, 1994, pp. 1087–1091, XP000456947.

Friedlander et al., "Nuclear and Radio Chemistry", $3^{rd}$ ed. John Wiley & Sons, New York; excerpt pp. 279–286, 1981.

Knoll, Glenn F., Radiation Detection and Measurement, John Wiley & Sons, New York; excerpts pp. 10–13, 363, 372–373, 395–396, 398–399, 402–403, 717–720 and Chapter 20 (p. 774–797), 1979.

"Webster's Ninth New Collegiate Dictionary", Merriam–Webster Inc., Springfield, MA USA, excerpt p. 315, 1990.

* cited by examiner

APPARATUS FOR IN-SITU THICKNESS AND STOICHIOMETRY MEASUREMENT OF THIN FILMS

This application is a divisional of co-pending application Ser. No. 08/914,822, filed on Aug. 20, 1997 now U.S. Pat. No. 6,342,265, the entire contents of which are hereby incorporated by reference and for which priority is claimed under 35 U.S.C. §120.

BACKGROUND OF THE INVENTION

The present invention relates to an apparatus and method for in-situ thickness and stoichiometry measurement of thin films made by, for example, molecular beam epitaxy, chemical vapor deposition, sputtering, plasma coating, etc.

The present high demand for electronic and optoelectronic devices, such as quantum well laser diodes (see, Kasukawa, N. Yokouchi, N. Yamanaka, N. Twai and T. Matsuda, Jpn. J. Appl. Phys. 34, L965, 1995) or optical modulators (see, R. Y.-F Yip, A. Aït-Ouali, A. Bensaada, P. Desjardins, M. Beaudoin, L. Isnard J. L. Brebner, J. F. Currie and R. A. Masut, J. Appl. Phys. 81, 1905 (1997) and references therein), have pushed the epitaxial requirements to precisions and reproducibility in alloy compositions and thickness to the monolayer level. One method for measuring growth rate in Molecular Beam Epitaxy (MBE) is Reflection High Energy Electron Diffraction (RHEED). This method relies on the intensity oscillations of the diffracted electron beam caused by variable coverage during a layer by layer growth. RHEED measures growth rate only at the beginning of growth as the oscillations die out quickly in practice. Moreover, this method is not applicable when growth proceeds by other mechanisms, such as step-flow mode, and is not useful for measurements with sample rotation. These restrictions limit the usefulness of RHEED for real time feedback control of MBE growth.

These considerations have led to developments in ellipsometry where the thickness of grown films is inferred from the changes in the optical reflectivity and thin film interference effect (see, C. H. Kuo, M. D. Boonzaayer, M. F. DeHerrera, D. K. Schroder, G. N. Maracas and B. Johs, J. Cryst, Growth, (to be published, 1997) and references therein). Kuo et al. (Id)., for instance, have achieved in-situ thickness control of AlAs/GaAs Distributed Bragg Reflector (DBR) structures with a 0.3% reproducibility. The method relies on dynamic model fitting of the optical spectra during growth, which is sensitive to the optical properties of the growing materials. These depend on both the thickness and composition of the material, and neglects the effects of scattering due to surface roughness (see, M. K. Nissen, C. Lavoie, S. Eisebitt, T. Pinnington and T. Tiedje, R. S. Goldman, K. L. Kavanagh and J. L. Hutter, Appl. Phys. Lett., 67,3744 (1995)). To install the system on an MEE chamber, one optical port is used for the light source and another port for the ellipsometer. To allow for ellipsometric measurements under sample rotation conditions, it is necessary that the substrate surface remain parallel to the sample rotation. To achieve this, Kuo et al. developed a wobble free substrate rotation mechanism (see, C. H. Kuo, M. D. Boonzaayer, M. F. DeHerrera, D. K. Schroder, G. N. Maracas and B. Johs, J. Cryst, Growth, (to be published, 1997) and references therein).

The present inventor has taken a different approach to in-situ thickness and growth rate measurements in MBE with the use of Alpha Particle Energy Loss Method (AEL) (see, Kelson, Y. Levy and E. Redmard, J. Phys. D: Appl. Phys. 28, 100 (1995); Kelson, Y. Levy, D. Racah, E. Redmard, M. Beaudoin, T. Pinnington, T. Tiedje and U. Giesen, J. Physc. D: Appl. Phys. 30, 131 (1997)). This approach is easier to implement than ellipsometry while providing absolute thickness measurements that do not depend on optical properties. The AEL method has already been implemented by the inventor of the present invention 5 off-line, with good results, for thickness and stochiometry measurements of several materials including semiconductors (see, Id.). It is an object of the present invention to provide a method and apparatus for on line, in situ implementation of the AEL method for the thickness and stoichiometry of thin films, particularly film made by Molecular Beam Epitaxy. It is a more particular object of the present invention to provide on line, in-situ implementation of the AEL method for the growth of III–V semiconductors, and other films with MBE.

SUMMARY OF THE INVENTION

In accordance with the above objects, the present invention provides an apparatus for measuring the thickness of films grown on a substrate in a growth chamber. The apparatus comprises: a protective housing having an aperture opening into the growth chamber, a solid state detector disposed in the protective housing, a shutter for opening and closing the aperture, a shield disposed in the housing between the aperture and the solid state detector for shielding the detector, and a calibration source disposed between the shield and the detector for calibrating the measurements made by the detector.

The apparatus also preferably comprises a second calibration source disposed between the shutter and the shield, for measuring deposition on the shield. A second shutter is provided for selectively exposing and containing the second calibration source.

A temperature detector is preferably positioned to detect the temperature of the protective housing and a cooling device is constructed to cool the housing.

In one preferred embodiment, a device for focusing said detector on one or more predetermined regions of the substrate is additionally provided.

Also in accordance with the above objects, the present invention provides a method for measuring a property of a film deposited on a substrate in a growth chamber comprising the steps of: implanting one or more alpha sources in a substrate, placing the substrate in a growth chamber, growing a film on the substrate, detecting the loss of energy of alpha emissions of the substrate as a film is grown on the substrate in the chamber with a detector, protecting the detector from the growth chamber with a shield, calibrating the detector with a calibration source disposed between the detector and the shield, and calculating the property of the film on the substrate using the loss of energy of the alpha emissions from the source.

The method preferably further comprises the step of calibrating the detector with a second calibration source to compensate for deposition on said shield from the growth chamber. The property measured is thickness of the film, stoichiometry of the film, or a combination of both.

In one embodiment, the step of detecting comprises detecting the loss of energy of two or more alpha lines. In a still further embodiment, the step of implantation comprises recoil implantation using an implantation source made by irradiation with a beam of $^{228}$Fr. In yet another embodiment, the step of implantation comprises recoil implantation using an implantation source made by irradiation with a beam of $^{227}$Fr.

The α-particle source is preferably selected from $^{228}$Th, or $^{227}$Th.

In another embodiment, the method further comprises the step of focusing the detector on or more predetermined regions of the substrate. In this embodiment one or more sources can be implanted in a predetermined pattern on the substrate.

Further objects, features and advantages of the present invention will become apparent from the Detailed Description of the Preferred Embodiments, when considered together with the attached drawings.

DETAILED DESCRIPTION OF THE PREFERRED EMBODIMENTS

The present invention provides a simple and practical method for determining simultaneously the local thickness and the local average stoichiometry of thin films, related to actual needs in specific technological applications (see, J. Geerk, G. Linke and O. Meyer, Materials Science Reports 4 (1989), 193).

When a charged particle moves through a medium it loses energy due to interactions with its constituents. This process has been extensively studied, formulated (see, H. A. Bethe and J. Ashkin, "Passage of radiation through matter," in Experimental Nuclear Physics, Vol 1, ed. By E. Segre (John Wiley & Sons, New York, 1953)) and tabulated (see, L. C. Northcliffe and R. F. Schilling, Nuclear Data Tables 7 (1970), 733; J. F. Ziegler and J. Biersack, "Code TRIM, the transport of ions in matter," Pergamon Press, New York 1985). The amount of energy lost depends on the identity of the charged particle, on its initial energy, on the identity of the medium and on the length of the trajectory traversed through it. In order for this phenomenon to be useful as a means for measuring the (average) thickness of a thin film, the initial and final energy spectra of the charged particle must be sufficiently well defined (see, I. Kelson, Y. Levy, D. Nir and P. E. Haustein, Jour. Of Phys. D 27 (1994), 1087). For a monoenergetic particle, the initial energy spectrum usually consists of a sharp, well-defined peak. The smaller the fraction of the initial energy lost by the slowing down particle, the better its final energy definition as well.

The present invention uses α-particles for a number of reasons: α-particles with a few MeV kinetic energy lose only a small fraction of their energy passing through films of a few microns; sources emitting monoenergetic α-particles in that range are available; it is practically easy to implant such sources in substrates on which thin films of technological importance are grown (see, I. Kelson, Y. Levy, E. Redmard, Jour. Of Phys. D 27 (1994), 1087). Thus, the method of the present invention comprises implanting α-emitting nuclei in a substrate, and then measuring the energy lost by the α-particles of well defined initial energy as they traverse a layer grown later on that substrate. By employing particle counting techniques with high enough statistics, very high precision measurements are possible. One embodiment of the invention utilizes $^{224}$Ra, implanted by the α-induced recoil of $^{228}$Th, and giving rise—through a sequence of decays—to a set of α-lines of various energies (8.78, 6.78, 6.29, 6.05 and 5.69 MeV) (see, C. H. Kuo, M. D. Boonzaayer, M. F. DeHerrera, D. K. Schroder, G. N. Maracas and B. Johs, J. Cryst, Growth, (to be published, 1997) and references therein).

This method of the present invention is conceptually related to the well known RBS (Rutherford Back Scattering). The present invention, however, comprises the measurement of the transmission of multiple monoenergetic α-particles through a thin layer, effectively with no support. Unlike RBS, all α-particles are effectively used so that a much smaller flux of particles passes through the layer. Since one only needs an unsealed "mother" isotope (in one embodiment $^{228}$Th, in other embodiments $^{227}$Ac) and a small vacuum system for marking, it is cheaper and simpler to implement.

A. Implantation

Implantation, or "marking" of the alpha-emitters is done using the natural recoil energy nuclei obtain upon decay. A primary radioactive species is placed on a surface (or slightly underneath it) which is referred to as the "source". This species decays by emitting alpha-particles, in the course of which the resultant nucleus (the "daughter") receives a substantial amount of recoil energy (of the order of 100 keV). This recoil energy is sufficient to implant the daughter at a depth of the order of a few tens of nanometers in any material. The daughter itself being an alpha-particle emitter, one thus achieves the objective of implanting a source of alpha particles in the substrate. The daughter itself, upon decaying, generates yet another alpha-emitting nucleus, and this process continues until a stable nucleus is formed. If a longer-lived nucleus appears in this decay chain, then it is possible to mark the surface by a two-stage process (rather than by a one-stage process). Namely, one implants the recoils from the primary species (the source) into an auxiliary substrate. Then one arranges for the subsequent recoils from that substrate to be implanted into the actual substrate.

B. Available decay chains

There are two main decay chains available for the proper implementation of the marking scenario, starting with the primary species $^{228}$Th and $^{227}$Ac respectively. They are the following (decay mode and half-life are indicated in parentheses):

$^{228}$Th (alpha, 1.9 y)→$^{224}$Ra (alpha, 3.7 d→$^{220}$Rn (alpha, 55 s)→$^{216}$Po (alpha, 0.15 s)→$^{212}$Pb (beta, 10.6 h)→$^{212}$Bi (beta, 1 h)→$^{212}$Po (alpha, 0.3 us) $^{208}$Pb (stable).

$^{227}$Ac (beta, 21.8 y)→$^{227}$Th (alpha, 18.7 d)→$^{223}$Ra (alpha, 11.4 d)→$^{219}$Rn (alpha, 4 s)→$^{215}$Po (alpha, 1.8 ms)→$^{211}$Pb (beta, 36 m)→$^{211}$Bi (alpha, 2.1 m)→$^{207}$Tl (beta, 4.8 m)→$^{207}$Pb (stable).

While both of the above species can be used for implantation, the actinium series has several advantages. For example, the implantation lifetime is longer.

The "228" chain permits marking with a 3.7 day half-life activity ($^{224}$Ra) using single stage or with a 10.6 hour half-life activity ($^{212}$Pb) using two stage marking. The "227" chain permits marking with a 11.4 day half-life activity ($^{223}$Ra) using single stage or with a 36-minute half-life activity ($^{211}$Pb) using two stage marking. Note, that in the case of one-stage marking the entire subsequent chain is present in the substrate.

C. Source Preparation

A number of options are available for the preparation of the primary source (namely, the surface with the initial species on it). A preferred method according to the present invention is to use a francium beam from an isotope on-line separator and to implant it in a suitable foil. To generate the "228" chain one implants $^{228}$Fr, which proceeds to decay as follows (main branch only):

$^{228}$Fr— (beta, 39 s→$^{228}$Ra— (beta, 5.76 y)→$^{228}$Ac (beta, 6.1 h)→$^{228}$Th.

The "228" chain source may also be prepared by radio-chemical separation of $^{228}$Th, as a compound, such as a nitrate, for example, and then fixing the $^{228}$Th to the surface of the marking source by electrodeposition followed by diffusion bonding. Other methods of fixing, such as firing, may also be used.

The francium beam method comprises producing and separating the Fr isotope in a separator, and then implanting the separated beam directly into a foil which then serves (after the subsequent decays to the desired isotopes) as the implantation source.

The Fr beam method has the advantages of being the only method presently capable of producing the "227" chain. Second, the source is ready in its final form. The radioactive nuclei are buried slightly under the surface, which makes the implantation source more robust. Third, the isotopes are carrier-free and are of high radiochemical purity. In the case of the "228" chain, one actually generates $^{228}$Th from $^{228}$Ra. The species $^{228}$Ra, with its 5.76 y half-life makes a much longer-lived source.

To generate the "227" chain one implants $^{227}$Fr, which proceeds as follows:

$^{227}$Fr (beta, 2.4 m)→$^{227}$Ra (beta, 42 m)→$^{227}$Ac.

D. The implantation setup

A setup designed and built to perform the implantation (marking) process described above will now be described. The system and its operation are so designed as to insure that none of the atoms of gaseous species in the decay chain (Rn) can come out of it.

Figure 5:
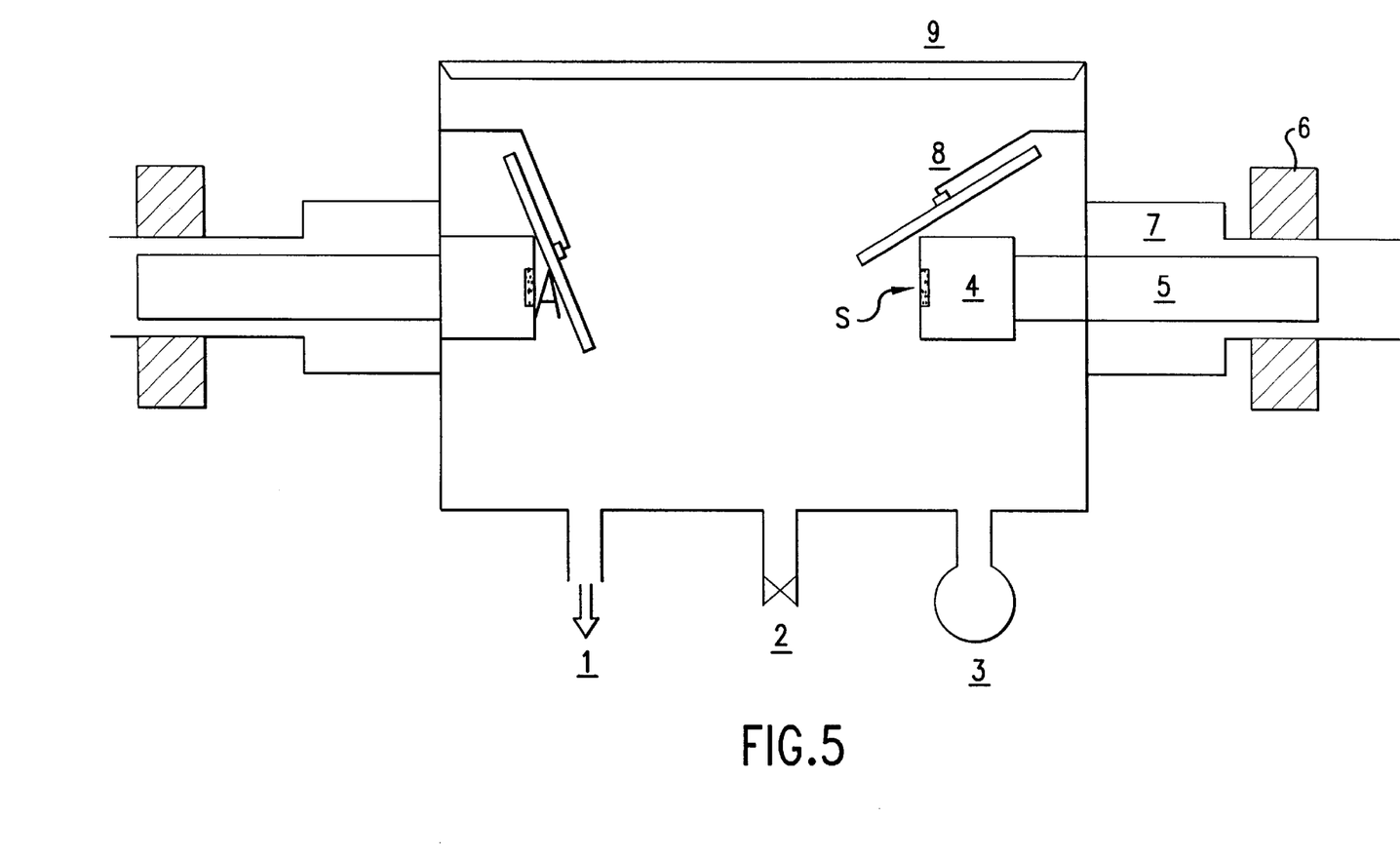
FIG. 5 is a schematic representation of the implantation setup according to the present invention.

The layout of the system is schematically shown in FIG. 5. The system is a small vacuum vessel, pumped (by a sorption pump) through inlet 1 with an air-inlet valve 2 and a vacuum gauge 3. The system has two identical holders 4, mounted on shafts 5 which can be moved by an external magnetic actuator 6. Each holder can be completely retracted into its enclosure 7, which is then automatically closed by a spring operated shutter 8. One holder is fitted with the primary source S, for example $^{228}$Th, and the other with the auxiliary surface A. A wafer can be inserted into the system through a normally sealed opening 9. The system is normally held under vacuum.

Marking the auxiliary surface is done by extending the two holders and bringing them close to each other. Normally, if this extends over periods longer than the $^{224}$Ra half-life, S and A are in equilibrium.

To mark a wafer with $^{224}$Ra, it is inserted into the system facing S.

To mark a wafer with $^{212}$Pb, it is inserted into the system facing A.

In both procedures the unused holder can be optionally stored in its enclosure.

The wafer is inserted into the system as follows. While the system is under vacuum the two holders 4 are retracted into their enclosures 7. The pressure is brought up by letting air in; this results in the pressure sealing of the enclosures. One waits for about 10 minutes, until all loose $^{220}$Rn [55 second half-life] activity has died, as a measure of added radiation safety. The wafer is inserted through its opening and the sealed system is once again evacuated.

Marking a substrate with the "227" chain, can be carried out in a similar manner to the "228" chain.

E. Thickness Measurements by AEL Method, Measurements and Calculations, and Examples The AEL method is described in detail in publications of the present inventor (see, I. Kelson, Y. Levy and E. Redmard, Jour. Of Phys. D 27 (1994), 1087). The present embodiments of the application of AEL to on line, in situ measurement of film thickness and stoichiometry will be described as follows.

Prior to insertion into the MBE, radioactive nuclei are recoil implanted into the substrates (for example, GaAs and InP) from a source, for example, $^{228}$Th. The implanted species are, for example, $^{224}$Ra (3.66 days half-life) as well as the nuclei resulting from the decay chain of the implanted species. Each of these nuclei emits an α-particle with a characteristic energy. As these emitted a-particles pass through a film of thickness X, they lose an average amount of energy $\bar{E}_{loss}$ (see, Kelson, Y. Levy and E. Redmard, J. Phys. D: Appl. Phys. 28, 100 (1995)):

$$\bar{E}_{loss} = X(dE/dX) \qquad (1)$$

where dE/dX is the characteristic energy loss per unit length for the film's material at that energy (see, Kelson, Y. Levy and E. Redmard, J. Phys. D: Appl. Phys. 28, 100 (1995)). Since dE/dX is known for each material (see, J. F. Ziegler and J. Biersack, Code TRIM, the transport of ions in matter", Pergamon Press, New York, N.Y., 1985), measuring $E_{loss}$ gives the thickness X directly (see, Kelson, Y. Levy and E. Redmard, J. Phys. D: Appl. Phys. 28, 100 (1995)). To get an absolute thickness measurement, one also needs to consider the system geometry as discussed below. The statistical uncertainty in thickness) X is related to the uncertainty in the measurement of the energy loss $\Delta \overline{E}_{loss}$ by (see, Kelson, Y. Levy and E. Redmard, J. Phys. D: Appl. Phys. 28, 100 (1995)):

$$\Delta X = \frac{\Delta \overline{E}_{loss}}{(dE/dX)} = \frac{\delta E}{(dE/dX)\sqrt{N}} \quad (2)$$

where $\delta E$ is the uncertainty of a single measurement and N is the number of counts collected. Systematic errors also need to be considered. These include instabilities in the α-particle detector, changes in the implanted source geometry, coverage of the detector by the growing species and uncertainties in the tabulated dE/dX values. Statistical uncertainties are significant for low levels of implantation.

To implement AEL for in-situ monitoring, an α-particle detector head is built and installed on a VG V80H MBE chamber through one of the shutter ports. A detailed description of the monitor is given below with respect to FIG. 6. In principle, any available port could be used provided that the detector looks directly at the sample and that the head assembly does not interfere with the molecular beams or other monitoring ports. The head is mounted with the detector at a distance of about 10 cm from the sample surface making an angle of 50° to the sample normal. In this geometry, the collection efficiency is 0.3%. A mechanical shutter in front of the detector head is opened or shut to measure the α-particle flux at will. In the growth chamber, the energy position of the α-lines are determined precisely before initiating growth. This is equivalent to an off-line measurement. During film growth, the detector shutter is periodically opened for thickness measurements. The sample is then measured again at the end of growth. The measurements are collected with a multi-channel analyzer (MCA) card and a Windows based acquisition program.

Figure 1:
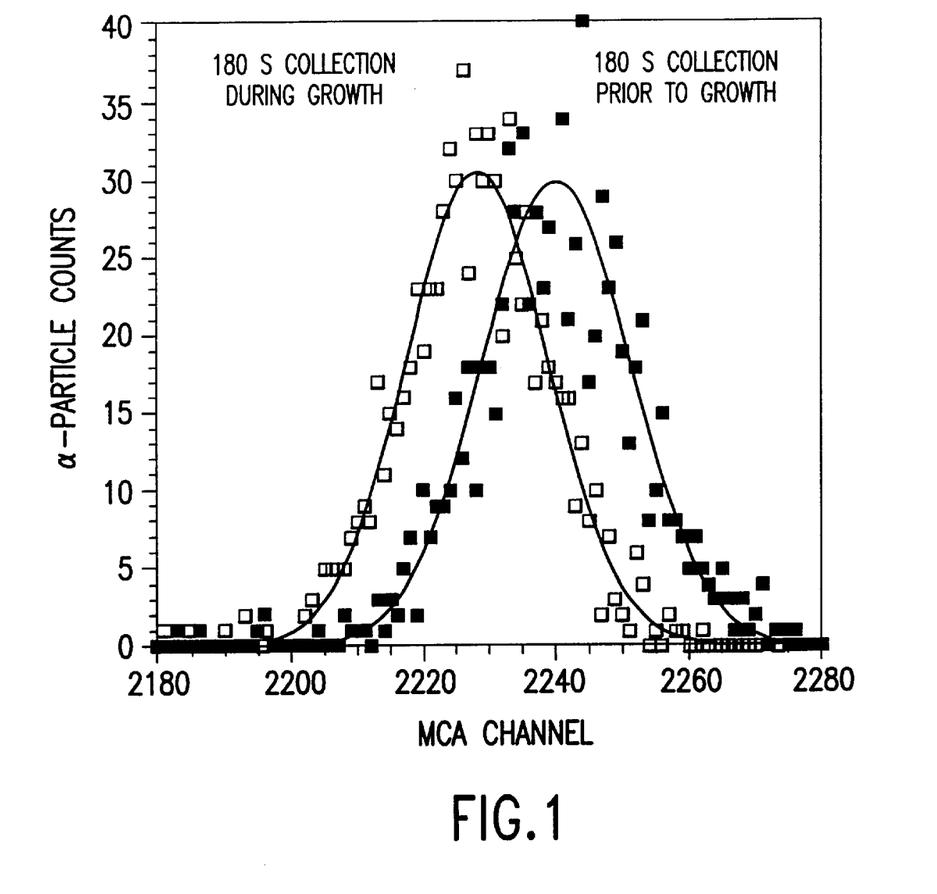
FIG. 1 is a superposition of two typical in-situ raw data showing counts against channel number. The higher energy peak, (higher channels) was taken just prior to growth initiation while the other peak, was taken by a 180 s measurement during the growth of an InP film.

In the present implementation, we are using a weak 0.3 $\mu$Ci source of $^{228}$Th to implant the substrate with 500–1500 Bq of $^{224}$Ra activity over a 5 mm diameter region (1 $\mu$Ci=3.7×10$^4$Bq–3.7×10$^4$ disintegration). This activity corresponds roughly to 10$^9$ nuclei/cm$^2$ distributed over a depth of 10–20 nm below the substrate surface. As a figure of merit, the density of interface states capable of storing charge at the Si/SiO$_2$ interface (MOS devices) is on the order of 10$^{10}$ per cm$^2$. For III–V heterojunctions the density of interface states is typically higher. In the GaAs/AlGaAs heterojunction for instance, the interface defect density is estimated at about 10$^{11}$/cm$^2$. Note, however, that the α-emitters are implanted in the substrates, therefore several 100 nm away from the active regions of typical device structures. Moreover, these substrates are generally either semi-insulating or heavily doped 10$^{18}$ cm$^{-3}$); in either case, the implanted nuclei will have no effect on the performance of devices. Finally, because of the 3.66 days half-life of $^{224}$Ra, the radioactivity has effectively completely died out within a period of a few weeks. In principle, any one of the emission lines, with their characteristic energies (5.686, 6.288, 6.779, 6.050 and 8.785 MeV), can be used for monitoring. For offline measurements, all emission lines are used. In the present set of in-situ measurements, we used, for convenience, the 8.787 MeV emission line of $^{212}$Po. FIG. 1 shows a superposition of two typical in-situ raw data (counts vs. Channel #) collected on the MCA and their gaussian fits (continuous lines). The higher energy peak (higher channel), corresponds to the 8.785 MeV α-emission line before growth. This provides a convenient "zero" of energy with a precision only limited by the statistical uncertainty. Note that the measurements are affected by material deposition on the detector during growth. This deposition manifests itself by a shift of the "zero" at the beginning of every growth. This "zero" was measured over several growths and showed a gradual but small shift with exposure time. We therefore neglect it in the present analyses. With the use of a stronger source, which means lower detector exposure during measurements, this effect will truly be negligible. The peak at lower energy comes from a measurement of 180 s during the growth of an InP film. The gaussian fit to the peaks gives both the energy position and its standard deviation $\delta E$. These energy losses are then transformed to film thickness via Eqs. 1 and 2 and the angle that the detector head makes with the sample surface. Using the "zero" and the tabulated dE/dX of the growing material, the MCA can be calibrated directly to thickness which allows real time monitoring.

Figure 2:
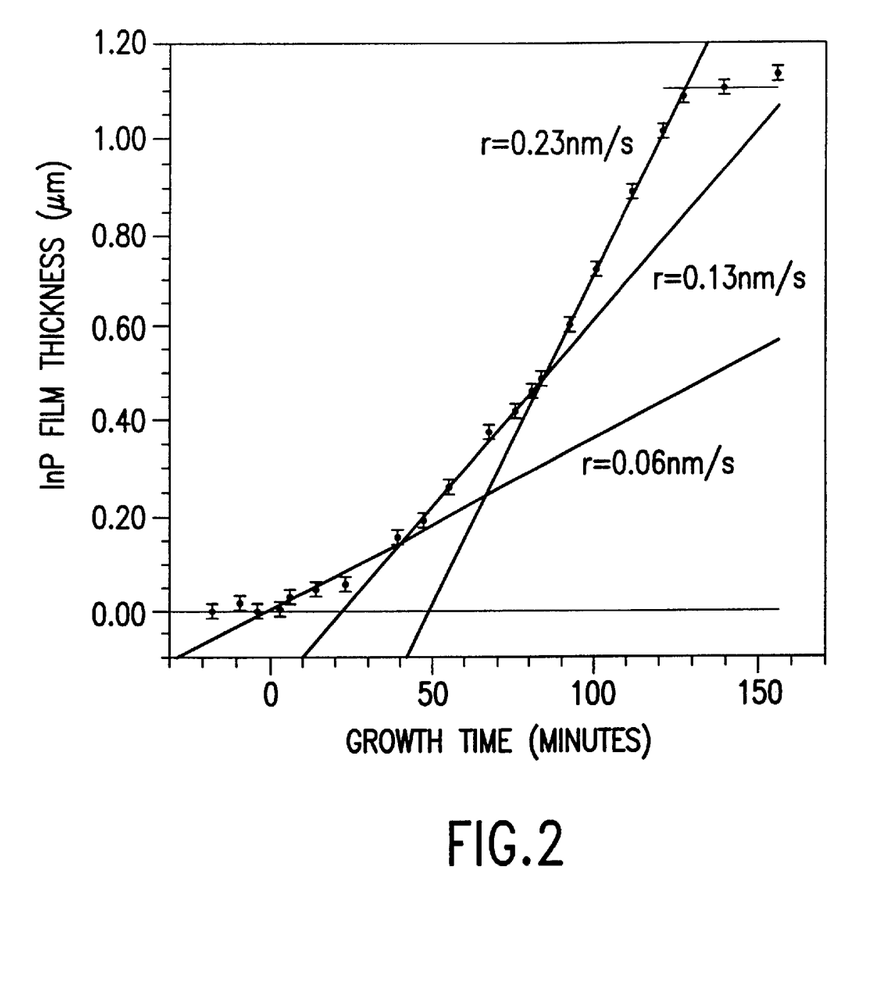
FIG. 2 shows in-situ thickness measurements as a function of time during the growth of an InP film (growth initiated at time=0). The data were taken by 180 s collection times of α-particles. The error bars show the thickness uncertainties of single measurements while the straight line fits show the 3 growth rate regions.

FIG. 2 shows a typical thickness versus time graph taken from the growth of an InP layer (growth begins at t=0). With the 500–1500 Bq of implanted activity, each measurement was 180 s in duration. About 800 α-particles were measured in each interval and the estimated uncertainty in thickness is ±6 nm. The accuracy on the growth rate determination is ±0.01 nm/S. The improvement is due, of course, to the statistical averaging of the least squares fit.

Figure 3:
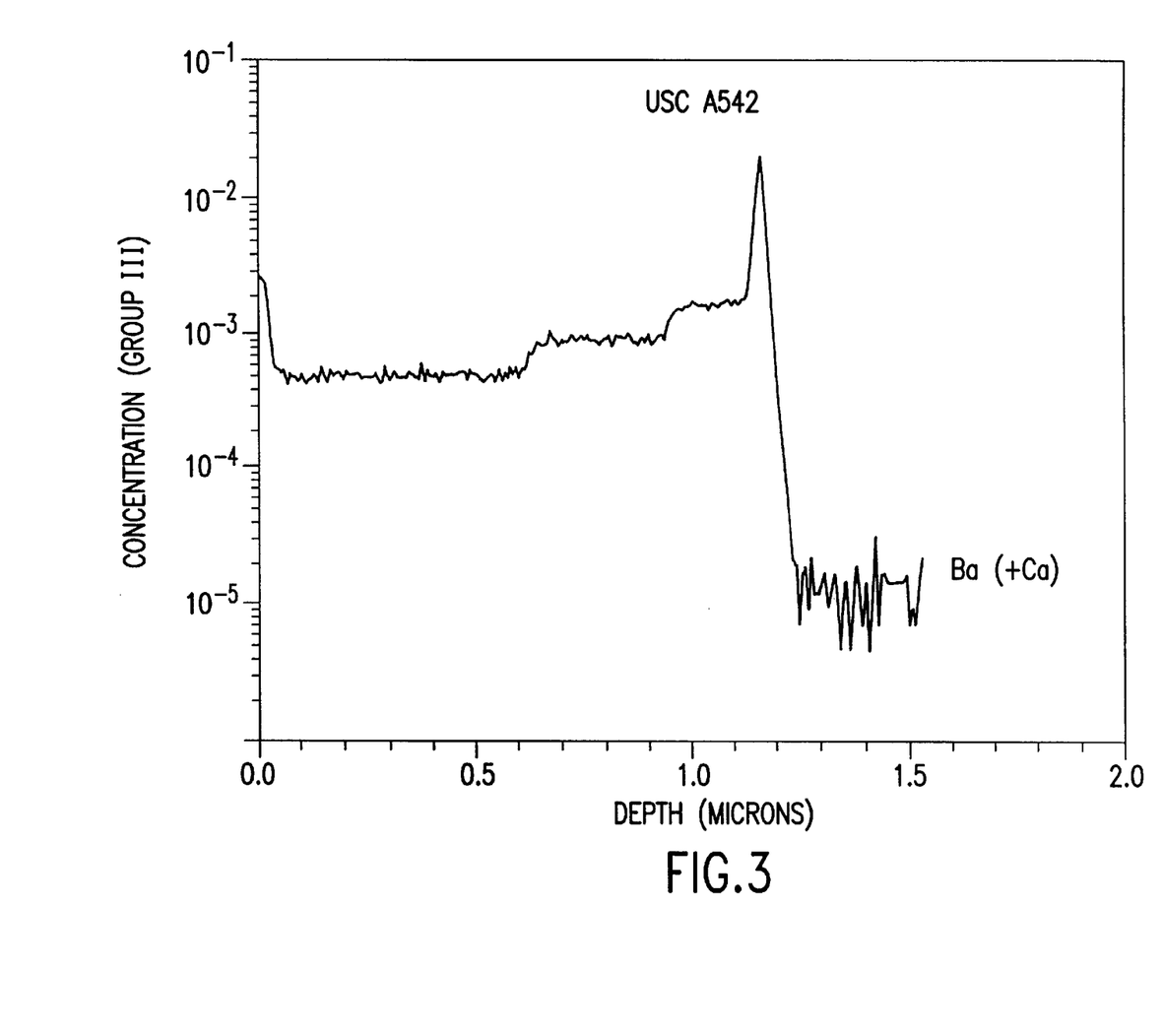
FIG. 3 is a SIMS spectrum of the InP sample of FIG. 2. The Ga concentration serves as thickness markers since the 3 regions were grown at different V–III ratios using a GaP source for phosphor.

As shown on FIG. 2, the InP growth rate was increased in 2 steps during the growth by changing the temperature of the In cell. The phosphorous source was polycrystalline GaP whose main contaminant is expected to be residual Ga. While the In cell temperature was changed during growth, we intentionally kept the GaP source temperature constant, effectively changing the V–III ratio. Hence, a Secondary Ion Mass Spectrometry (SIMS) spectrum of the residual Ga in the film serves as thickness markers. FIG. 3 shows the SIMS profile of this InP sample. The agreement between the SIMS and AEL results are within a few percent for the three growth rate regions. The difference can be attributed to the uncertainties in the SIMS measurements and the exact detector head vs. sample geometry. Offline thickness measurements are generally in better agreement (about 2%) with other thickness determinations (X-ray diffraction and electron microscopy) but still indicate a need for improved energy loss tables (dE/dX).

Figure 4:
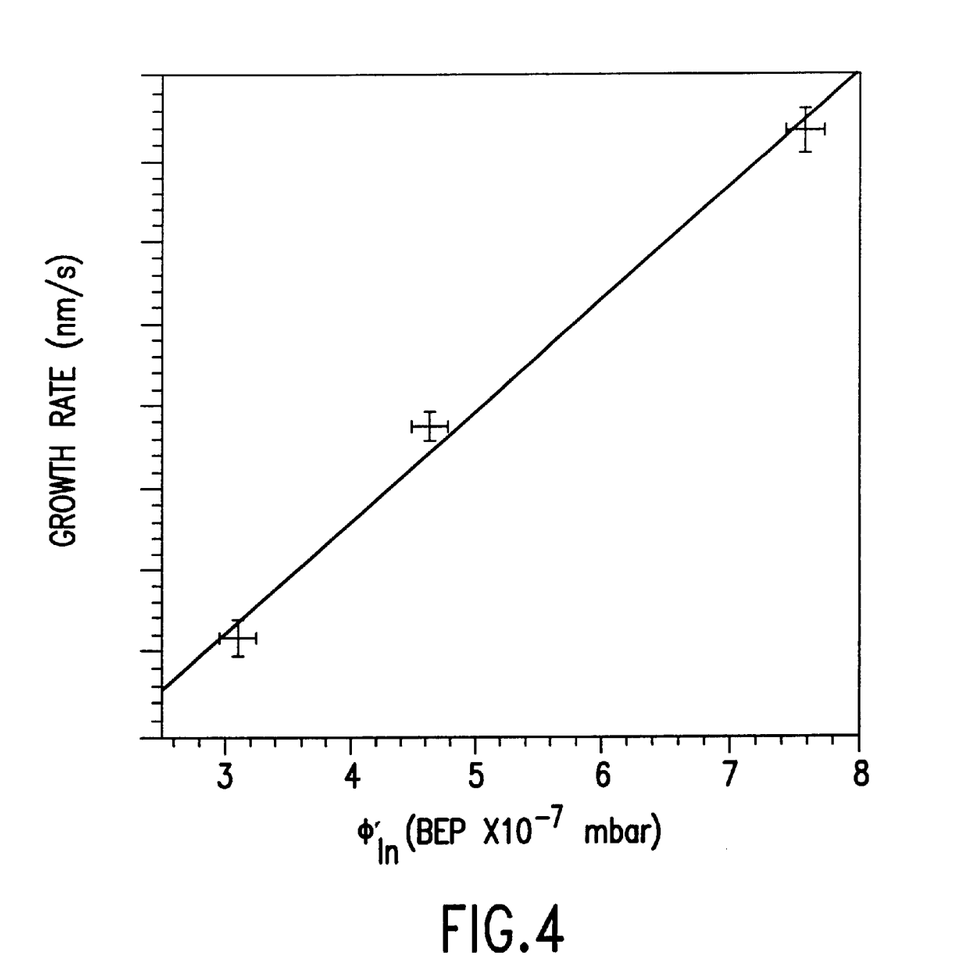
FIG. 4 is the AEL determined growth rate of the InP sample against calibrated In flux. The rate is linear with flux but does not extrapolate to the origin. This indicates one use of AEL as a growth control tool.

FIG. 4 shows the InP growth rate determined by AEL against the calibrated In flux $J_{In}$. The linear relationship between growth rate and flux is expected. In MBE, the growth rate is proportional to both the group III flux and the sticking coefficient at a given substrate temperature. The AEL method allows a direct measurement of the growth rate from which one can also determine the sticking coefficient in a single growth run. This is an advantage over the conventional method which uses a flux calibration and several growth runs to determine the growth rates and sticking coefficients. To illustrate this point, notice that the line fit to the rate vs. $J_{In}$ plot does not extrapolate to the origin. One explanation is that the rate is not linear at very low growth rates, which would be the case if, for instance, the sticking coefficient was dependent on the material flux. If this is the case, the AEL becomes a valuable tool to study fundamental growth mechanisms. The more likely explanation however, is that the true In flux during this growth was lower than its calibrated value due to material depletion the effusion cell since the last calibration.

The basic operational parameter which determines the inherent statistical uncertainty of an individual measurement is the total number of usable α-particles counted. This number, N, is a product of the counting time $t_{meas}$ and the counting rate Γ. In this work, where very weak α doses were used, longer measurements ($t_{meas}$=180 s) were performed by way of compensation. Note however, that the measured thickness value corresponds to the mean time of the measurement. By the time this information is available (at the end of data taking), the film will have grown an additional thickness T.

$$T = \frac{1}{2} r t_{meas} \tag{3}$$

where r is the growth rate of the film. For a measurement to be truly instantaneous, the additional amount grown on the film during the measurement should clearly not exceed the statistical uncertainty of the measurement itself. For each experimental scenario we may define the basic thickness resolution $\Delta X_0$ (and its corresponding basic measuring time $t_0$) by demanding the measurement uncertainty and the actual thickness increment to be equal.

$$\Delta X_o = \frac{\delta E}{(dE/dX)\sqrt{\Gamma t_o}} = r t_o \tag{4}$$

Eliminating $t_0$, one obtains the following useful operational relationship between resolution and counting rate:

$$\Delta X_0 = \left[ \frac{\delta E}{dE/dX} \left( \frac{r}{\Gamma} \right) \right]^{\frac{1}{3}} \tag{5}$$

Limiting the overall α-emitter dosage to sub-μCi level and assuming realistic growth and monitoring parameters $\Delta X_0$ in the 1 to 3 nm range can be reasonably expected.

It must be stressed that $\Delta X_0$ represents the uncertainty of a single, independent, absolute thickness measurement, which can be performed at any time during growth. Obviously, two (or more) such measurements can be combined to yield values of the growth rate. The more separated in time the two measurements are, the more accurate is the (average) rate determination. A particularly relevant monitoring scenario involves a series of L consecutive measurements, each with its $\Delta X_0$ uncertainty. Assuming the growth rate to be constant during this time span, the thickness uncertainty $\Delta X_f$ at the end of the sequence can be shown to be given by:

$$\Delta X_f = 2\Delta X_0/\sqrt{L} \tag{6}$$

Thus, sub-nanometer and even monolayer accuracy in endpoint determination can be reasonably expected.

The primary objective of the present work was to demonstrate the ability to perform in-situ thickness measurements during film growth in MBE. In the present implementation, we have achieved a thickness accuracy of ±6 nm with a growth rate accuracy of ±0.01 nm/s for typical growth rates of 0.3 nm/s or less. According to theoretical estimates, these numbers are expected to improve with the use of a stronger primary source. The AEL method is qualitatively simple. Although more calibration work is still necessary, it seems to provide quantitatively useful information on film growth.

F. Stoichiometry Measurements in Thin Films, Measurements, Calculations, and Examples As with the example of film thickness measurement discussed above, the central physical measurement is dE/dX, the energy lost per unit length in a medium of charge Z, density ρ and mass number A. In this example, it is more convenient to express the thickness of the medium as the number of atoms (in mols) per unit area, ν, and to define the stopping power S(E,Z) as the energy loss rate of an α-particle of energy E per unit ν. Thus, $$S(E, Z) \equiv \frac{dE}{dv} = \frac{A}{\rho} \cdot \frac{dE}{dX} \tag{1}$$

The (average) thickness νz of a layer of material of charge Z is simply given by $$vz = \frac{E_{loss}}{S(E, Z)} \tag{2}$$

where $E_{loss}$ is the (average) energy lost by the α-particles. There are two corrections which are made in this example: (1) the change in S(E,Z) with energy is taken into account self-consistently with the degradation of energy from E to E–$E_{loss}$; and (2) the geometric dispersion of path lengths is averaged over, when, as in the present example, a finite size detector is used to measure the given embedded source.

In converting the film's overall measured stopping power to its thickness in this case one assumes S(E,Z) to be known. S(E,Z) can be phenomenologically determined without recourse to any specific theoretical modeling. However, if the film is composed of more than one element, and the relative abundance of its constituents is not actually known, this simple conversion is not possible. The situation is analogous to that occurring in the usage of one oscillating quartz crystal for measuring the thickness of a multi-element deposit.

Additional information under these circumstances can be obtained by measuring the slowing down of α-particles of a different energy, E'. In actuality, when sources are implanted in substrates as discussed above, α-particles of more than one energy are indeed emitted during the decay sequence of the embedded $^{224}$Ra. If α-particles of two different initial energies, E and E', are measured concurrently, then one obtains a set of two linear equations $$E_{loss} = \sum_i S(E, Z_i) \cdot vz_i \quad E'_{loss} = \sum_i S(E', Z_i) \cdot vz_i \tag{3}$$

Where the summation runs over all elements present in the film. Thus, if the film is composed of two different elements, $Z_{1x}Z_{2(1-x)}$, the quantities of both elements can be independently determined by the method of the present invention.

The approximate functional structure of S(E,Z) is such, that only two linearly independent constraints on the densities $v_{Zi}$ can be obtained even when more than two α-lines are measured. Thus, when the film contains more than two elements, the individual values of $v_{Zi}$ cannot be determined. However, these two constraints are useful by providing necessary, though not sufficient conditions, for two films to have identical thickness and composition.

The ratio between the stopping powers at the two energies, can be defined as follows $$R_{E'E}(Z) = S(E', Z)/S(E, Z) \tag{4}$$

and the ratio of energy losses can be rewritten as $$\frac{E'_{loss}}{E_{loss}} = \frac{\sum_i R_{E'E}(Z_i) \cdot S(E, Z_i) \cdot vz_i}{\sum_i S(E, Z_i) \cdot vz_i} \equiv \overline{R_{E'E}(Z)}. \quad (5)$$

The entity $\overline{R_{E'E}(Z)}$ is clearly related to the composition of the film. In the specific case of the binary compound $Z_{1X}Z_{2(1-X)}$ there is a direct correspondence between $\overline{R_{E'E}(Z)}$ and the stoichiometry parameter x—$\overline{R_{E'E}(Z)}$ varies between $R_{E'E}(Z_2)$ and $R_{E'E}(Z_1)$ as x varies between 0 and 1. The experimental uncertainty in the measurement of x is thus given by the formula $$\Delta \chi \approx \frac{\Delta \overline{R}}{|R(Z_1) - R(Z_2)|} \approx \frac{\Delta E_{loss}}{|R(Z_1) - R(Z_2)|E_{loss}} \quad (6)$$

where numerical factors of order unity as well as the energy subscripts, have been omitted where they are self understood.

(1) Stoichiometry Measurement Example

The following example describes measurements of the stoichiometry related ratio $\overline{R}$ in accordance with the present invention. This example does not calculate absolute values of $\overline{R}$ with high precision, but precision can be improved depending on a number of factors including setup geometry, calibration line characteristics and data analysis procedures. This example treats the various physical systems using identical scenarios, thereby obtaining an estimate of the useful range of $\overline{R}$ as a source for stoichiometric determination.

The films grown in the example were chosen so as to cover a range of generic compositions: Sb on Si—a pure, single element; GaAs, InAs and AlAs on GaAs—a series of binary III–V type compounds of structurally well defined stoichiometry; $YBa_2Cu_3O_{7-\delta}$ on YSZ (Yttrium Stabilized Zirconium) substrate—a multi-component film whose approximate stoichiometry can be inferred from its high-$T_c$ superconducting properties.

(2) Experimental Procedure

The measurements comprised the following steps: Each substrate over which the film was to be grown was routinely prepared for insertion into the growth chamber. A few nanocuries of $^{224}Ra$, the α-emitting source, were implanted into the substrate over an area of about 0.2 $CM^2$. The areal density is thus in the range of $10^8$–$10^9$ atoms per $cm^2$ and the average implantation depth, as calculated by TRIM (see, J. F. Ziegler and J. Biersack, "Code TRIM, the transport of ions in matter", Pergamon Press, New York, 1985), is about 30 nm. The implantation procedure was conducted according to I. Kelson, Y. Levy and E. Redmard, Jour. Of Phys. D 27 (1994), 1087. The amount of implanted material can be chosen arbitrarily and controllably over a large range. The a-spectrum of each bare substrate was measured in a dedicated vacuum chamber using a standard silicon detector.

(i) The marked substrates were introduced into the growth chamber where the layer was grown. YBCO was grown in situ on a heated substrate by RF sputtering from a stoichiometric target in an argon-oxygen atmosphere. This procedure was conducted in accordance with C. B. Eom, J. Z. Sun, B. M. Lairson, S. K. Streiffer, A. F. Marshall, K. Yamamoto, S. M. Anlage, J. D. Bravman, T. H. Geballe, S. S. Laderman, R. C. Taber and R. D. Jacowitz, Physica C 171 (1990), 354. In the case of Sb, the evaporation was done from an ohmically heated boat over an unheated substrate. The III–V compounds were grown by molecular beam epitaxy with substrate temperatures ranging up to 600° C. It was verified that the implanted α-particle sources (e.g. $^{224}Ra$) do not diffuse in the different substrates over which the films were grown, at the temperature conditions of the various growth procedures. Using a mask, a portion of marked substrates was kept in its bare form for subsequent comparison and calibration.

(ii) The α-spectra of the samples were measured again in the dedicated chamber. These measurements were carried out in conjunction with both the bare samples and with a $^{241}Am/^{244}Cm/^{239}Pu$ α source for calibration. Care had to be taken to reproduce the geometric layout of the sample-counter ensemble. The FWHM of the measured α-lines varied from about 30 keV for bare lines to about 110 keV for the lines most shifted in energy.

Figure 7:
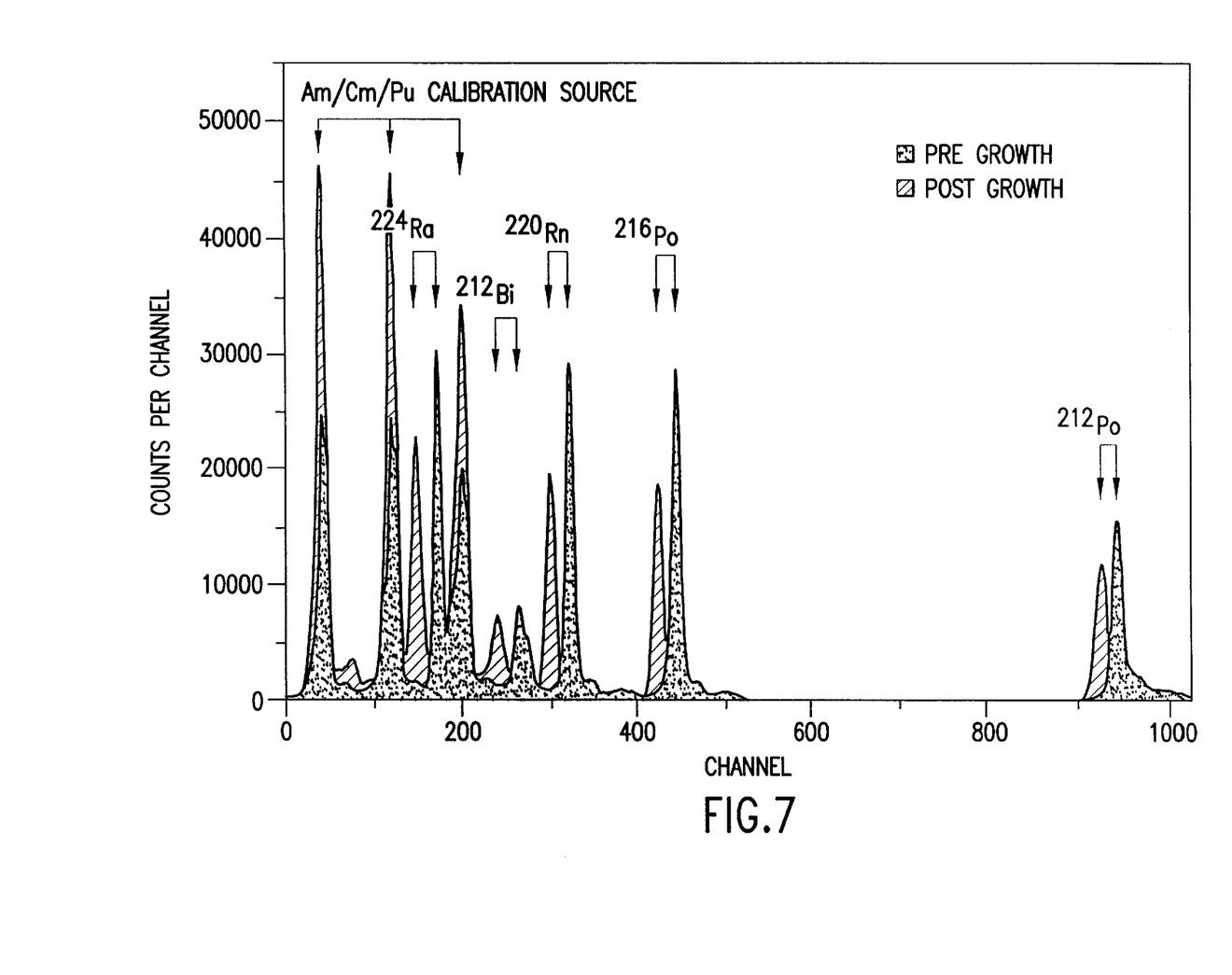
FIG. 7 shows the pre-growth and the post-growth α-particle energy spectra in the measurement of the stoichiometry of YBCO, superposed on each other. The constant Am/Cm/Pu calibration lines are shown, as well as the shifts of the lines from the implanted source, caused by the YBCO layer. The net area of the peaks varies between 200,000 and 600,000 counts.
Figure 8:
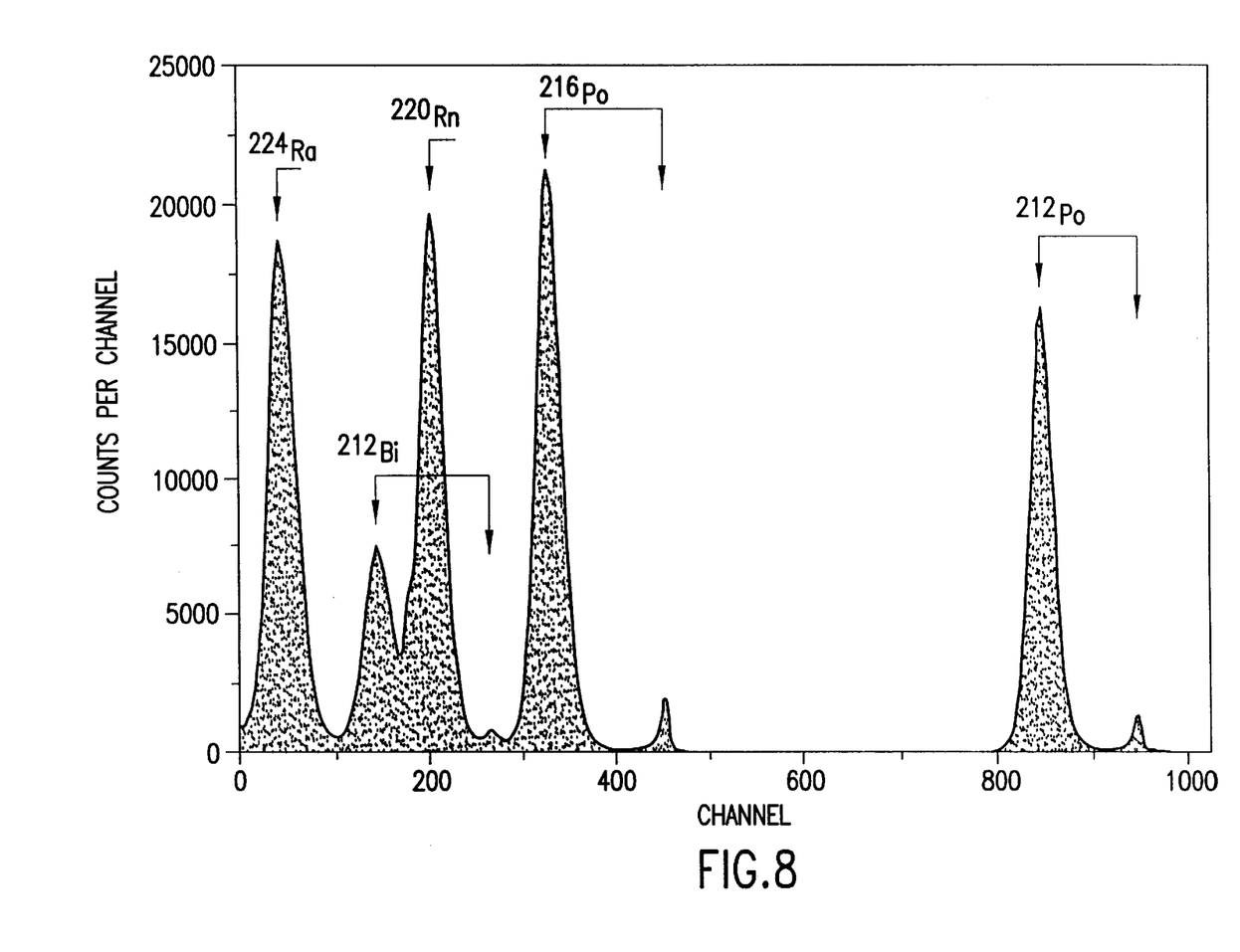
FIG. 8 shows the α-particle energy spectrum in the measurement of film thickness and stoichiometry using Sb (without the Am/Cm/Pu calibration lines) showing both the pre-growth (from the masked area) and the post-growth lines. The post-growth lines have a net area of 150,000 to 550,000 counts. The pre-growth lines are about a factor of 20 weaker, but their FWHM is smaller by about a factor of 3. The pre-growth lines of $^{224}$Ra and $^{220}$Rn in this particular spectrum coincide with stronger shifted lines and cannot be resolved.

Sample α-particle energy spectra obtained will be described with reference to the Figures. FIG. 7 shows the pre-growth and the post-growth spectra in the YBCO case, both with the $^{241}Am/^{244}Cm/^{239}Pu$ calibration source, superposed on each other. FIG. 8 shows a typical α-particle energy spectrum, where both the pre-growth (from the masked portion of the substrate) and the post-growth components were measured concurrently (here, the Sb case). The position (in channels) of each of the peaks was determined by a multiple Gaussian fit. Energies and energy differences were subsequently evaluated by using the ensemble of available calibration lines.

Table 1 gives the measured energy loss of the 5.69-MeV α-line of $^{224}Ra$ for one each of the different types of film grown. Since this is the first line in the series of α-decays and because it has the lowest energy it is most suitable for the thickness determination. Using standard stopping power tables (see, J. F. Ziegler and J. Biersack, "Code TRIM, the transport of ions in matter", Pergamon Press, New York, 1985) and assuming Bragg's law to hold for the common stoichiometry of each material, these energy losses are converted to the thickness values shown in the Table. The appropriate corrections (the variation of S(E,Z) with energy and the geometric dispersion of path lengths) have been applied in this conversion. Errors in this case are not assigned to the thickness because of the unknown systematic errors in the tabulated values of S(E,X), which are considered to be of the order of a few percents. There is, however, an intrinsic high precision (0.1% and better) associated with the nuclear aspect of the measurement. The quoted uncertainties are actually larger (typically by a factor of 2 to 2.5) than what would be expected from pure statistical considerations (see, e.g., C. M. Lederer and V. S. Shirley, eds., Table of Isotopes $7^{th}$ Ed. (Wiley Interscience, New York, 1977) This is the source of nuclear data used in the example.) This is primarily due to deviations from the exact Gaussian nature of the peaks.

TABLE 1

| Material | $E_{loss}$ [keV] | Thickness [micron] |
| --- | --- | --- |
| Sb | 529.11 ± 0.28 | 2.444 |
| GaAs | 284.97 ± 0.19 | 1.339 |
| InAs | 196.29 ± 0.14 | 0.934 |
| AlAs | 246.26 ± 0.15 | 1.140 |
| YBCO | 96.74 ± 0.10 | 0.369 |

The energy lost by the $^{224}Ra$ 5.69-MeV α-particles in traversing films of the different materials of the examples, and the thickness of those films obtained by the use of standard energy loss tables. No errors are assigned to the thickness because of unknown systematic errors involved in the conversion.

TABLE 2

| Material | $\overline{R}_{6.29,5.69}$ | $\overline{R}_{6.78,5.69}$ | $\overline{R}_{8.29,5.69}$ |
|---|---|---|---|
| Sb | 0.9411 ± 0.0007 | 0.8935 ± 0.0007 | 0.7547 ± 0.0006 |
| GaAs | | 0.8962 ± 0.0010 | 0.7622 ± 0.0009 |
| InAs | | 0.8981 ± 0.0009 | 0.7634 ± 0.0009 |
| AlAs | | 0.8884 ± 0.0008 | 0.7423 ± 0.0008 |
| YBCO | 0.9284 ± 0.0013 | 0.8728 ± 0.0013 | 0.7162 ± 0.0012 |

The observed ratios of the energy loss of various α-lines to the energy loss of the $^{224}$Ra 5.69-MeV α-line for the different films of the Example. Some entries are missing because of incidental overlap of shifted and unshifted (calibration) lines. The weaker 6.05-MeV line of $^{212}$Bi is omitted from the Table because of its composite nature (containing a 6.09-MeV component) and poorer statistics.

Figure 9:
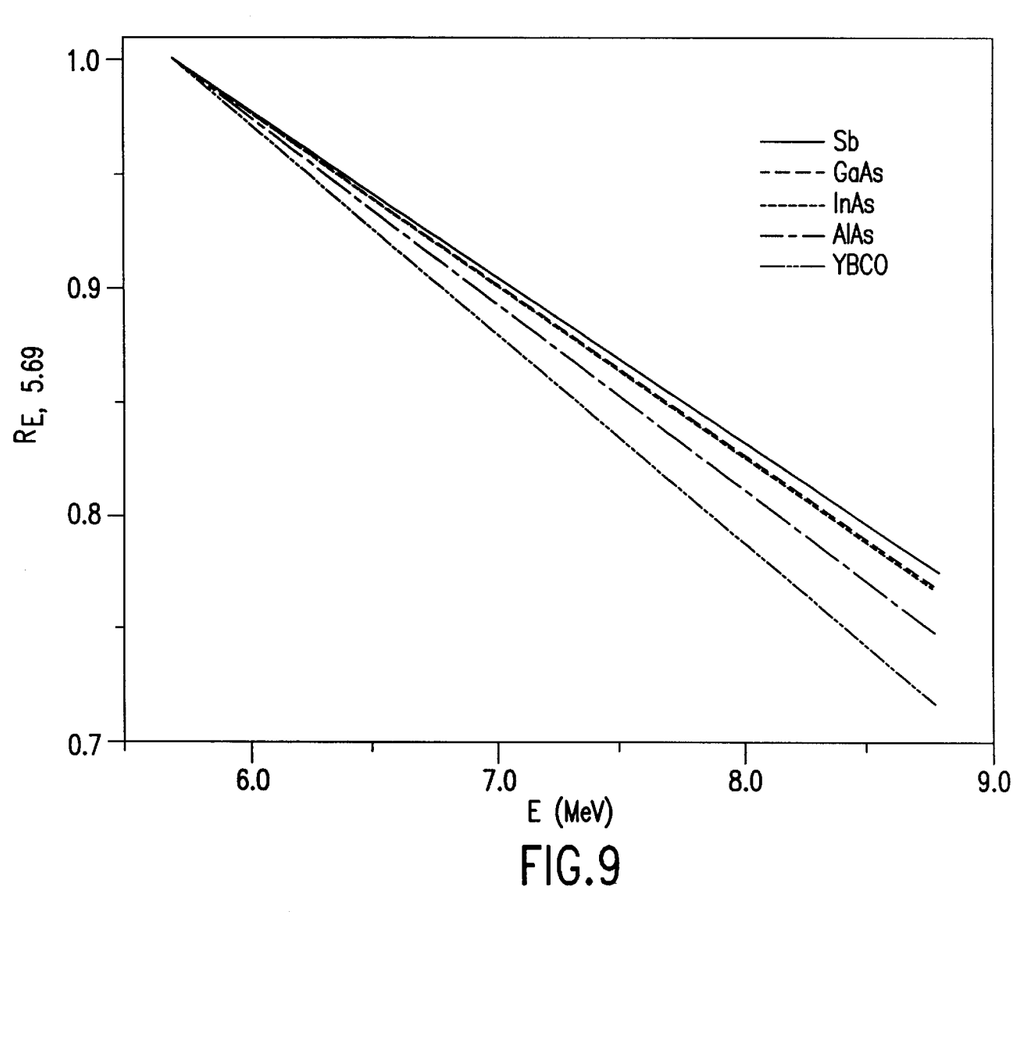
FIG. 9 shows a schematic linear fits to $\overline{R_{E,5.69}}$, the ratio of energy losses of α-particles of initial energies E and 5.69 MeV respectively, as a function of E, for the various materials measured according to the method of the present invention. Correction taking into account the variation of $\overline{R_{E,5.69}}$ with thickness (due to the non-linear dependence of $S(E,Z)$ on E) was applied to the experimental values of Table 2, as is described below.

Table 2 presents, for the same films, the energy loss values of additional α-lines expressed as the stoichiometric related ratio $\overline{R(Z)}$. A number of uncertainties, which enter into the determination of absolute energy loss values, clearly cancel out when ratios of such values are formed. The subscripts of $\overline{R}$ refer to the initial energies of the corresponding α-lines. The values of $\overline{R}$ actually depend on the thickness of the layer, since $E_{loss}$ is not linear in E. Thus, to provide a meaningful comparison between different measurements, those values should be extrapolated to zero thickness of S(E,Z). To illustrate schematically the implication of (the extrapolated) $\overline{R(Z)}$ to stoichiometry, we plot in FIG. 9 linear fits to its dependence on energy for the various materials. It is the slope of these curves which is the experimental entity related to the film's identity and stoichiometry.

The experimental values of $\overline{R_{E,5.69}}$ for Sb and for the GaAs/InAs/AlAs compounds agree rather well (to about 1%) with the ratios extracted from the standard tables, using Bragg's law. This is not the case for YBCO, where the experimental curve is steeper by about 5% than the corresponding theoretical value. This may be a consequence of the particular structure of YBCO. In any case, it demonstrates the need to base any stoichiometric information extracted from $\overline{R}$-values on actual experimental calibration.

The method for measuring the thickness of thin films and for obtaining stoichiometric information according to the present invention is discussed above. The usefulness of this method is, of course related to the accuracy of the measurements.

The uncertainties in the measured quantities are directly related to the uncertainty $\Delta E_{loss}$ in the energy loss values. If the measurement of $E_{loss}$ involves N counts, namely N statistically independent α-particle energy measurements, then its pure statistical uncertainty $\Delta E_{loss}$ is given by $$\Delta E_{loss} \propto \frac{\Delta E}{\sqrt{N}} \qquad (7)$$

where ΔE is the uncertainty of the individual measurement. A number of statistically independent factors contribute to ΔE. They include the intrinsic resolution of the detector, the distribution of initial depths of the implanted α-sources, the variation of path lengths through the film and the dispersion of the energy loss itself. The intrinsic detector resolution is constant, amounting to a (minimal) contribution of 5–10 keV to ΔE(12–25 keV FWHM), and is the dominant factor for sufficiently thin films. The number of counts N is given simply by $$N = \Gamma_{\alpha \cdot e \cdot t_{meas}} \qquad (8)$$

where $\Gamma_\alpha$ is the α-activity rate, ε—the counting efficiency and $t_{meas}$—the length of the measurement. Note, that unless one deals with actual real time growth monitoring, there is no intrinsic limitation on the length of measurement, aside from the trivial one imposed by the natural lifetime of the radioactive source. Due to energy straggling, the width of the observed α-lines increases for thicker films as they are shifted downward in energy. This width, which is dominated initially by the intrinsic resolution of the counter, is gradually determined by real physical and geometric effects. The determination of $\overline{R}$, however, actually improves with thickness since the uncertainty in it is inversely proportional to the energy loss value.

The first scenario of interest involves the determination of the stoichiometry parameter x in the ternary compounds $Al_xGa_{1-x}As$, $In_xGa_{1-x}As$ and $Al_xIn_{1-x}As$. This determination is based on an appropriate interpolation between the measured $\overline{R}$ values for the pure compounds GaAs, AlAs and InAs. These might be supplemented by additional measurements of intermediate x structures, which—in conjunction with independent methods—provide a detailed mapping of $\overline{R}$ into x. The uncertainty of x in this potential application may be estimated directly from the results of the example. The $\overline{R}$-curves for GaAs and for InAs are almost identical, implying that gallium and indium cannot be distinguished from one another by the method of the present invention. By contrast, there is a dispersion of about 3% between the corresponding $\overline{R}$-values for GaAs and AlAs. For films which are at least 1 micron thick, assuming energy loss measurements of accuracy similar to that reported here, x can be determined with an uncertainty of approximately 1%. Clearly, no unambiguous stoichiometry can be inferred for quaternary compounds AlGaInAs.

The fact that YBCO has more than two elements prohibits an unambiguous determination of its exact material composition, namely, of $n_y$, $n_{Ba}$, $n_{Cu}$ and $N_o$, the number of each species in a unit cell. Furthermore, since only one measurement of $\overline{R}$ was performed so far, it is impossible to determine directly at this stage its actual range of variation. Nevertheless, the method of the present invention can be used to estimate how $\overline{R}$ depends on each of the elements making up YBCO by using the theoretical stopping power tables as a first order approximation. This yields the following partial derivatives.

$$\frac{\partial \overline{R}}{\partial n_o} \approx 0.003 \qquad (9)$$

$$\frac{\partial \overline{R}}{\partial n_{Cu}} \approx 0.004$$

$$\frac{\partial \overline{R}}{\partial n_Y} \approx -0.009$$

$$\frac{\partial \overline{R}}{\partial n_{Ba}} \approx -.009$$

$\overline{R}$ is hardly sensitive to copper, since the stopping power S(E,Z) of copper behaves similarly to that of the entire compound. The sensitivity to oxygen, is smaller relatively to the heavier metals yttrium and barium because of its lower stopping power. According to these estimates, the uncertainty in the $\overline{R}$ curve actually measured for the 0.37-micron YBCO film (FIG. 7) would translate to an uncertainty of ±0.7 in $n_o$, if $n_o$ were the only variable parameter. This is not very useful, resulting primarily from working with a relatively thin film. For films in the range of 1–1.5 microns (or for thinner films measured obliquely) and with α-particle energy loss values determined with accuracy closer $\overline{R}$ to the pure statistical limit (eq. 7) the resolution in $n_o$ can be easily reduced to below ±0.1.

The main source of systematic error in converting an α-particle energy loss value to absolute film thickness is the uncertainty in S(E,Z). This error can be reduced, when necessary, by performing preliminary calibration measurements on the relevant materials in conjunction with additional, independent thickness and stoichiometry determinations. Thus careful application of the method of the present invention can be used to calculate useful stoichiometric information on deposited thin films. The stoichiometric evaluation can be conducted either "offline" or in situ during film deposition by molecular beam epitaxy.

G. Apparatus for In Situ Measurement of Film Thickness and Stoichiometry

To perform thickness measurements in real time, one must be able to operate the alpha particle detector in the growth chamber environment and to assure that the results obtained are accurate enough. This example provides a detector system actually designed, built and operated in a Molecular Beam Epitaxy machine.

Figure 6:
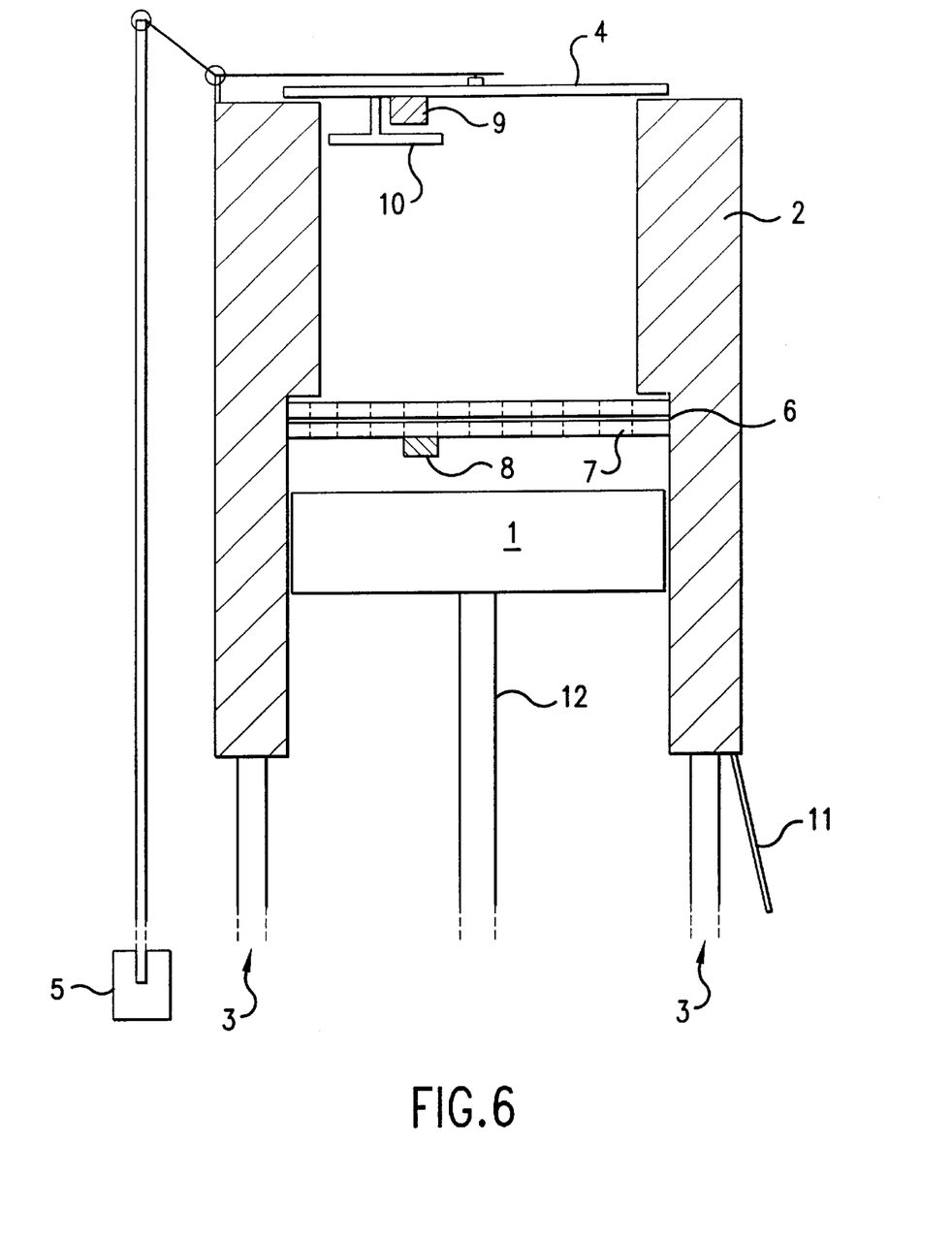
FIG. 6 is a schematic representation of the detector assembly used in the method and apparatus according to the present invention.

The detector assembly is schematically shown in FIG. 6. A solid state detector 1 (bakable to the required temperature; for example, at least about 2000 C.) is held in an enclosed, protective housing 2. The housing can be cooled (or heated) by means of a looping pipe 3 through which water or air can be passed. A shutter 4 normally closes an aperture in the housing. It can be opened or shut by means of an actuator 5 controllable from outside the vacuum (growth) chamber. In front of the detector, inside the housing, is a special shield 6. The shield is made of a thin, sub-micron aluminum foil, which reflects light and thermal radiation, blocks the passage of molecules and atoms, but permits the transfer of alpha particles with minimal degradation. In this embodiment, the Al film preferably has a thickness of about 0.7 g and the mesh 7 that mechanically supports the film has a transmission efficiency for alpha particles of 80–90%. The shield protects the detector from heat, radiation and light from the growth chamber. Although aluminum foil is proposed in this embodiment, one of ordinary skill in the art will understand that other foils can be utilized. The shield, which is too thin to support itself reliably, is held by a solid mesh 7.

A special alpha source 8 is placed between the shield and the detector, providing continuous calibration and control of the detector and its support electronics. A different alpha source 9 is placed between the shutter and the shield. This source is used to measure the amount of material which may have deposited on the shield during its exposure (namely, when the shutter is open for measurement). This source is protected by a mini-shutter 10, which closes by mechanical coupling when the (main) shutter is opened. This is done to ensure that no material deposit is formed on the shield-calibrating source itself. The temperature of the detector housing is monitored by means of a thermocouple wire 11. The electronic signal from the detector is extracted by means of a protected co-axial cable 12.

To operate the system one opens the shutter and takes an alpha particle spectrum. By comparing the energy loss of the alpha particles relative to the previous measurement the growth rate can be determined. By comparing it to the initial value, the total thickness is determined. As discussed above, by measuring the energy loss of two or more alpha lines, stoiciometric information can be gained from the sample. Some material may deposit on the shield during the opening of the shutter. To correct for this, the shield thickness change is measured with its calibration source before and after each opening of the shutter.

While the present invention has been described by means of several preferred embodiments, one of ordinary skill in the art will recognize that additions, deletions, substitutions and improvements can be made while remaining within the spirit and scope of the appended claims.

Specifically, while the examples of the present invention focus on measuring film thickness by molecular beam eptitaxy, one of ordinary skill in the art will recognize that the method is just as well applied to thin films made by other processes such as chemical vapor deposition, sputtering, plasma coating, etc.

Also, while the examples disclose methods of measuring film thickness in deposition processes, the method of the invention is also applicable to the measurement of film thickness during removal of material, such as by etching, for example.

What is claimed is:

1. An apparatus for measuring the thickness of films grown on a substrate in a growth chamber, comprising:

a protective housing having an aperture opening into the growth chamber, a solid state detector disposed in the protective housing, a shutter for opening and closing the aperture, a shield disposed in the housing between the aperture and the solid state detector for shielding the detector, the shield permitting the passage of α-particles and blocking the passage of other radiation, a calibration source disposed between the shield and the detector for calibrating the measurements made by the detector.

2. An apparatus according to claim 1, further comprising a second calibration source disposed between the shutter and the shield, for measuring deposition on the shield.

3. An apparatus according to claim 2, further comprising a second shutter for selectively exposing and containing the second calibration source.

4. An apparatus according to claim 1, further comprising a temperature detector positioned to detect the temperature of said protective housing and a cooling device constructed to cool the housing.

5. An apparatus according to claim 1, further comprising a device for focusing said detector on one or more predetermined regions of said substrate.

* * * * *